United States Patent [19]

Flanagan et al.

[11] Patent Number: 5,081,012
[45] Date of Patent: Jan. 14, 1992

[54] WAVEGUIDE SENSOR WITH INPUT AND REFLECTING GRATINGS AND ITS USE IN IMMUNOASSAY

[75] Inventors: Michael T. Flanagan, Bishop's Stortford; Andrew N. Sloper, London, both of England

[73] Assignee: Applied Research Systems ARS Holding N.V., Curacao, Netherlands Antilles

[21] Appl. No.: 435,519

[22] Filed: Jan. 22, 1990

[30] Foreign Application Priority Data

Mar. 29, 1988 [GB] United Kingdom ............... 8807486

[51] Int. Cl.$^5$ .................... G01N 33/53; G01N 21/00; G01N 21/76; C12M 1/40
[52] U.S. Cl. ................. 435/7.9; 435/7.92; 435/7.93; 435/7.94; 435/288; 435/291; 422/82.11; 356/73.1; 436/172
[58] Field of Search ............. 356/128, 73.1; 435/291, 435/288, 7.1, 7.9, 7.92, 7.93, 7.94; 422/59, 82.09, 82.11; 436/172, 518, 524, 582

[56] References Cited

U.S. PATENT DOCUMENTS 4,815,843 8/1989 Tiefenthaler et al. ............ 356/128
4,880,752 11/1989 Keck et al. ....................... 422/59

FOREIGN PATENT DOCUMENTS 3723159 1/1988 Fed. Rep. of Germany ...... 356/128
60-236006 11/1985 Japan ................................. 356/128
86/07149 12/1986 World Int. Prop. O. .......... 356/128

OTHER PUBLICATIONS

Bohn, P. W. in Trends in Anal. Chem., 6(9), pp. 223-233 (1987).
Tiefenthaler and Lukosz in Optics Letters, 10(4), pp. 137-139 (1984).
Fisher Catalog '86 Cat. #08-757-XXX.

Primary Examiner—David l. Lacey
Assistant Examiner—William Chan
Attorney, Agent, or Firm—Stephan P. Williams

[57] ABSTRACT

Waveguides suitable for use in optical assay techniques are described, as well as methods of assay employing such waveguides. The waveguide comprises an input grating structure to couple excitation radiation into the waveguide, a reflecting grating structure to reflect the excitation radiation propagating within the waveguide, and a transduction region located between the two grating structures, whereby during use the excitation radiation traverses the transduction region at least twice.

18 Claims, 7 Drawing Sheets

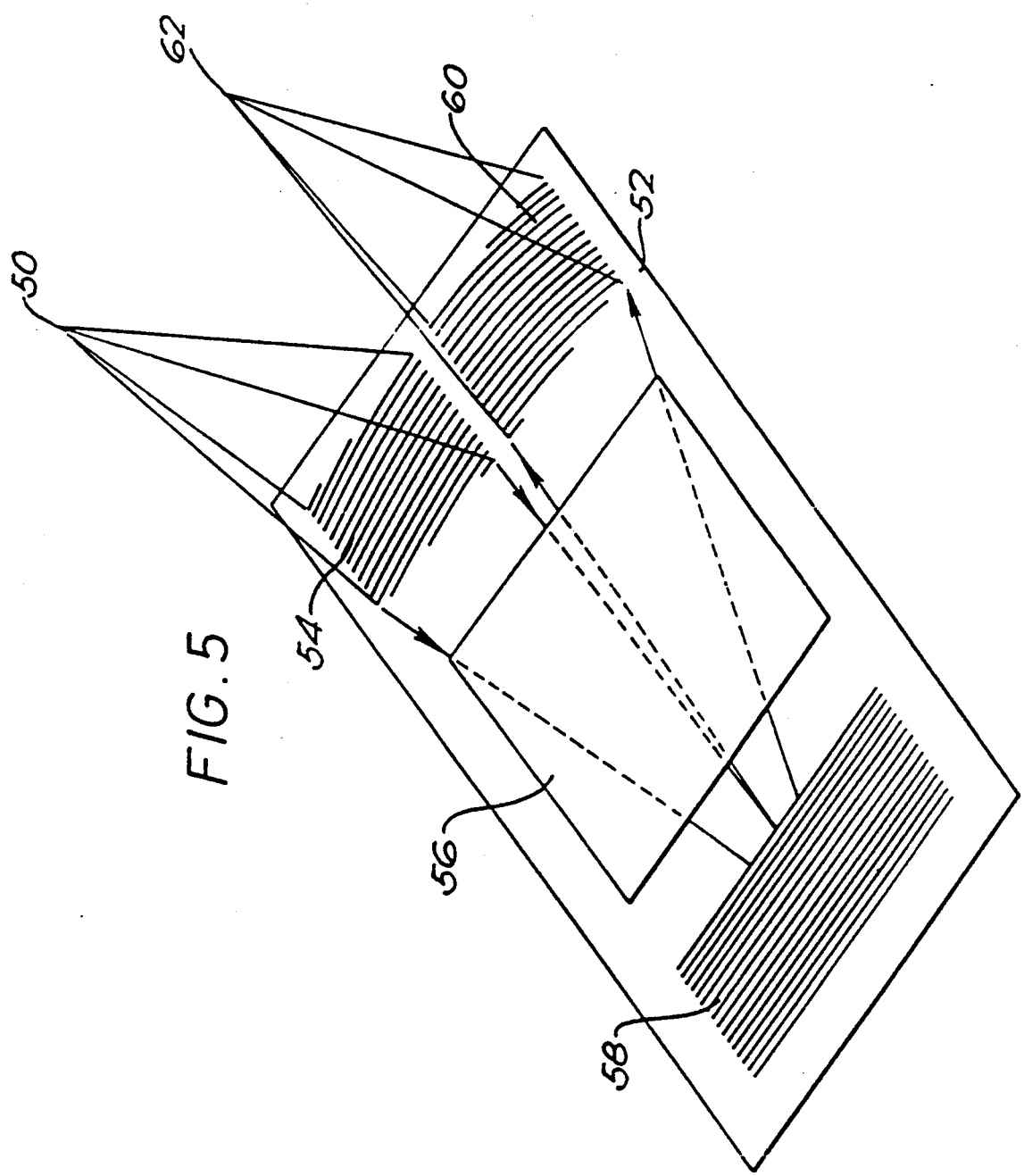

WAVEGUIDE SENSOR WITH INPUT AND REFLECTING GRATINGS AND ITS USE IN IMMUNOASSAY

This invention relates to waveguide sensors. More particularly this invention relates to waveguides for use in optical assay techniques for the qualitative or quantitative determination of chemical, biological or biochemical substances. The invention is particularly relevant to optical assay techniques using evanescent field excitation and/or detection.

In the prior art the use of evanescent methods to excite appropriate reagents has required the use of bulk optical components and/or fibre-waveguides.

The present invention involves the use of grating structures to provide signal enhancement functions not available in the prior art.

In its broadest aspect the invention provides a waveguide having at least one grating structure and at least one transduction region, the said waveguide being configured such that, in use, electromagnetic radiation propagating along the said waveguide interacts separately with at least one grating structure and at least one transduction region.

This invention concerns the use of grating structures to provide various functions for signal enhancement which were not available in the prior art. The principles of coupling gratings to low-order waveguides are known in the art. Gratings on optical waveguides of this type will typically have a pitch of 0.5 to 1.0 micrometer and a depth of the order of 100 nm. Such gratings will ideally have a sawtooth profile, but may have other profiles: for example, a substantially sinusoidal profile.

The functions that can be performed by the grating structures include input/output-coupling, spatial deformation of wavefronts and filtering according to differences in wavelength, polarisation or mode. The waveguide sensors of the present invention can employ one or more grating structures with the same or differing functions to produce a system capable of operating in the desired manner. The invention provides for great flexibility in the design of the sensor systems. The sensor system design may be optimised so as, for example, to provide maximum sensitivity or reliability. The use of grating structures to provide optical functions such as described above also allows the optical systems which are required to recover data signals from the sensor to be reduced in complexity and cost. The grating structures may be provided by a number of methods including, for example, modulation of the thickness or refractive index of the waveguide or its cladding. Some of such methods are particularly suited to low cost mass production techniques.

As explained above the grating structures can give rise to a large number of optical functions and it is envisaged that the interaction mentioned above between the electromagnetic radiation and the grating structure(s) includes all such functions. A given optical function may be performed by different grating configurations and the invention includes the use of all configurations which may be used to provide the desired optical function. Suitable configurations of grating structures for achieving a variety of functions will be apparent to those skilled in the art.

The invention is applicable to many different sorts of waveguide (e.g. a microscope slide) but according to a preferred feature of the invention the waveguide is a thin-film waveguide (e.g. having a thickness of 0.2–10 micron). Such thin-film waveguides have the advantage of having fewer possible modes thus making easier the control of the electromagnetic radiation propagating along the waveguide. In use, thin-film waveguides generally give rise to a more uniform evanescent field.

When used in assays of chemical, biological or biochemical substances the waveguide will have at least one transduction region with a material immobilised thereon, directly or indirectly, which material is capable of specifically binding with a species to be assayed. Examples of the types of materials that may be immobilised onto the transduction region include antibodies and antigens but the devices of the present invention are not restricted to devices for use in immunoassays. Also included are devices for use in other assays of biological, biochemical or chemical substances; the material immobilised on the transduction region will be an appropriate binding partner for the ligand under assay.

The design of waveguide gratings which act as filters and/or reflectors is known in the art; see, for example, D. Flanders et al, Appl. Phys. Letts. 1974, 194–196.

Thus, the waveguides may be such that, in use, the, or at least one, grating structure reflects said radiation. The provision of such an optical function increases the number of possible configurations of the sensor. One particular preferred configuration is such that the radiation is reflected so as to traverse the, or at least one, transduction region at least twice thereby increasing the intensity of said radiation within said region and reducing variation in the intensity of said radiation within said region. Such a configuration improves the performance of the sensor.

Another possibility is that in use, the, or at least one, grating structure filters said radiation in dependence upon the wavelength, polarisation or mode of said radiation. Again the provision of such an optical function increases the number of possible configurations of the sensor. An example of the use of such an optical function arises when using a waveguide in which the interaction of the radiation with the transduction region causes fluorescence and the, or at least one, grating structure differentiates between the stimulating radiation and the fluorescence. Since the wavelength of the output signal radiation is different from the stimulating radiation such a sensor has enhanced sensitivity. Various compounds which display fluorescence and may be disposed on or adjacent to the transduction region will be generally known to those skilled in the art. Examples of such compounds include coumarins, fluoresceins, lucifer yellows, rhodamines, phycobiliproteins and erythrosin.

In use, it is also possible for the, or at least one, grating structure to input- or output-couple said radiation. This feature is of advantage as it simplifies, makes more reliable, and makes less expensive to fabricate the means by which radiation is coupled to the sensor.

The waveguides may be such that, in use, the, or at least one, grating structure spatially deforms the wavefronts of said radiation. Once again the provision of such a feature increases the number of possible configurations of the sensor. The grating structure(s) may be such that, in use, the, or at least one, grating structure focuses, defocuses or collimates said radiation. By using an appropriate grating structure a large variety of deformations may be produced. The details of the methods of design of such grating structures are known in the art (see, for example, S. Ura et al, Proc. Optical Fibre Sensors Conference 1986, 171-174 and S. Ura et al, J. Lightwave Technology 1028-1033 (1988)).

A particularly advantageous embodiment is one in which, in use, the, or at least one, grating structure input-or output-couples the radiation to a focal point outside the waveguide. Such an embodiment has the advantage of removing the need for a number of additional optical elements external to the sensor.

In another advantageous embodiment, the waveguide is configured such that, in use, the focusing of said radiation serves to reduce variation in the intensity of said radiation between illuminated points, thus enhancing the performance of the sensor.

Another possible feature is that, in use, different wavelengths of said radiation are input- or output-coupled at different angles to said waveguide. This feature allows light of differing wavelengths to be simply and effectively separated.

According to some simple and effective preferred embodiments the waveguide may be planar and also possibly circular. The planar circular geometry lends itself to the provision of multiple transduction regions and can also be used to exploit the intensity profile of a focused beam to even out variations in radiation intensity due to absorption effects. However, the invention is not restricted to such geometries and also extends to non-planar waveguides.

It is also possible that a single grating structure may be used to provide more than one of the various optical functions described above.

The invention also extends to the use in an assay of a waveguide according to the invention.

For use in assays, an appropriate assay reagent will be immobilised on the surface of the transduction region(s). This reagent will be such that during the course of the assay, it inter-reacts with another component of the assay in such a way as to give an optically measurable result. For example, for use in an immunoassay of a ligand in a sample, the immobilised reagent may be a specific binding partner to the sample ligand. If there is present mixed with the sample a ligand analogue, labelled with a fluorophore (the term ligand analogue being used to denote a species capable of complexing with the same specific binding partner as the ligand under assay, including the ligand under assay itself) then a competition assay can be effected in which the amount of ligand analogue (and therefore the amount of sample ligand) can be determined by detection and measurement of the fluorophore label which becomes immobilised as a result of complex formation. Alternatively, where the sample ligand is multiepitopic, a sandwich assay may be performed by incubating the sample together with a specific binding partner (immobilised on the surface of the transducer) for the ligand under assay and together also with a second specific binding partner, the second specific binding partner being labelled with a fluorophore. On complex formation, the fluorophore label can be detected and the assay thereby determined.

It will be appreciated that the aforementioned assay protocols are mentioned by way of example only. Other assays which can be conducted using waveguides according to the invention will be readily apparent to one skilled in the art and the invention extends to such assays.

The waveguides of the present invention have particular applicability to immunoassays, in particular to the assay of antigens, including haptens, but also may find use in other specific binding assay procedures.

The invention also provides a method of assay for a ligand in a sample which method comprises incubating, simultaneously or in any desired sequence, the sample together with (a) a specific binding partner for the ligand it is desired to detect and (b) a further reagent, being either a ligand analogue or a specific binding partner of said ligand, one of components (a) or (b) being immobilised, directly or indirectly, on the surface of a transduction region of a waveguide as described hereinbefore and the other of components (a) or (b) carrying a fluorescent label; and determining whether, and if desired the extent to which and/or rate at which, the fluorescent label becomes indirectly immobilised on the said transduction region as a result of complex formation.

The invention further provides a method of assay for a ligand in a sample which method comprises incubating, simultaneously or in any desired sequence, the sample together with (a) a specific binding partner for the ligand it is desired to detect and (b) a further reagent, being either a ligand analogue or a specific binding partner of said ligand, one of components (a) or (b) being immobilised, directly or indirectly, on the surface of a transduction region of a waveguide as described hereinbefore and the immobilised component (a) or (b) or the surface of the transduction region carrying a fluorophore; and the other of components (a) or (b) being such that on complex formation the fluorescence of said fluorophore is quenched; which method includes the step of determining whether, and if desired the extent to which and/or rate at which, the fluorescence of said fluorophore is quenched as a result of complex formation.

The fluorescence may be filtered and/or collimated, if desired, before being detected by conventional means, for example one or more photomultiplier tubes.

Specific embodiments of the invention will now be described, by way of example only, with reference to the accompanying schematic drawings wherein.

Figure 3A:
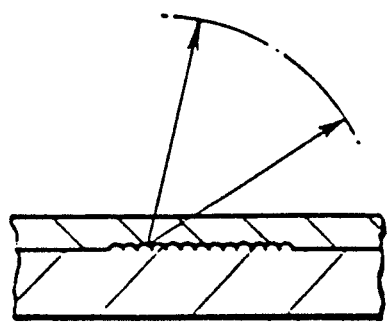

FIGS. 3(a), (b) and (c) show waveguides with grating structures which focus the radiation.

Figure 4:
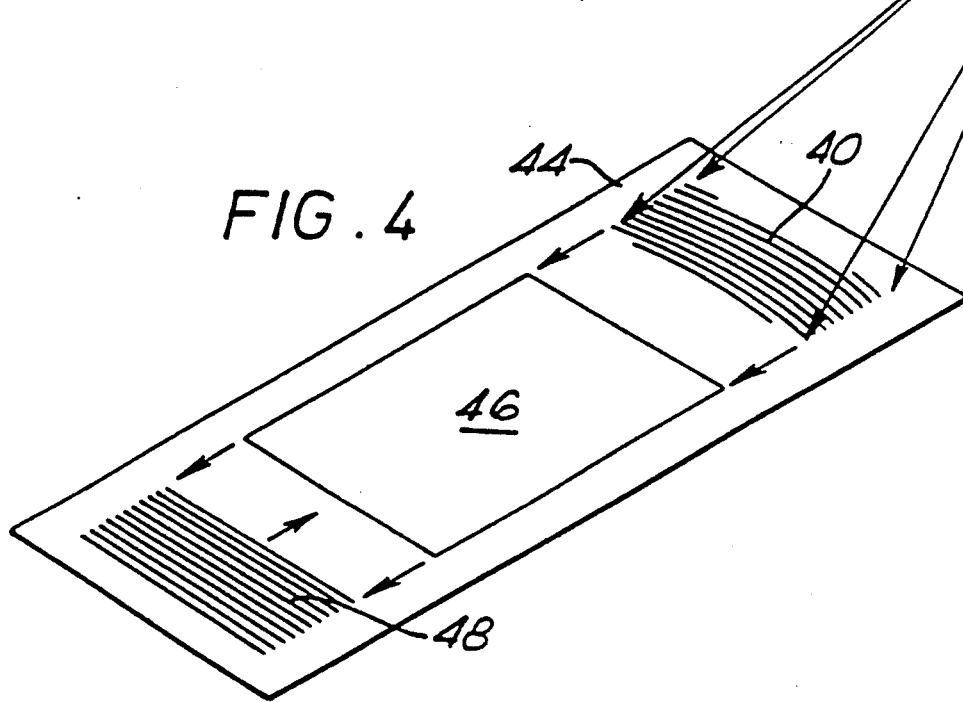

FIG. 4 shows a waveguide with simplified input/output coupling using a wavefront-deforming grating structure.

Figure 6A:
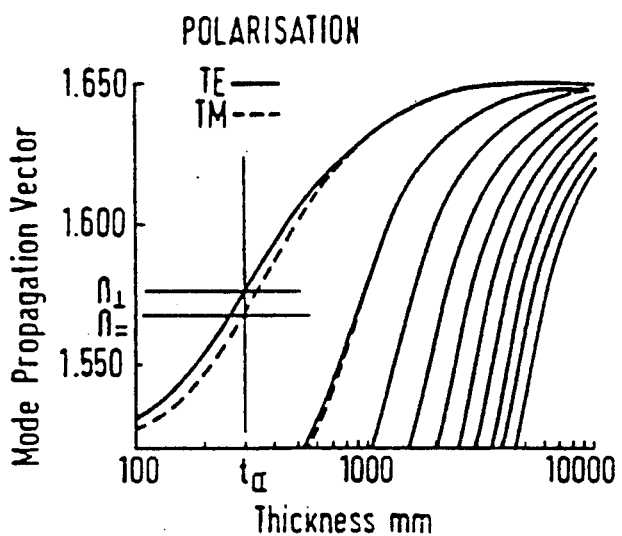
Figure 6B:
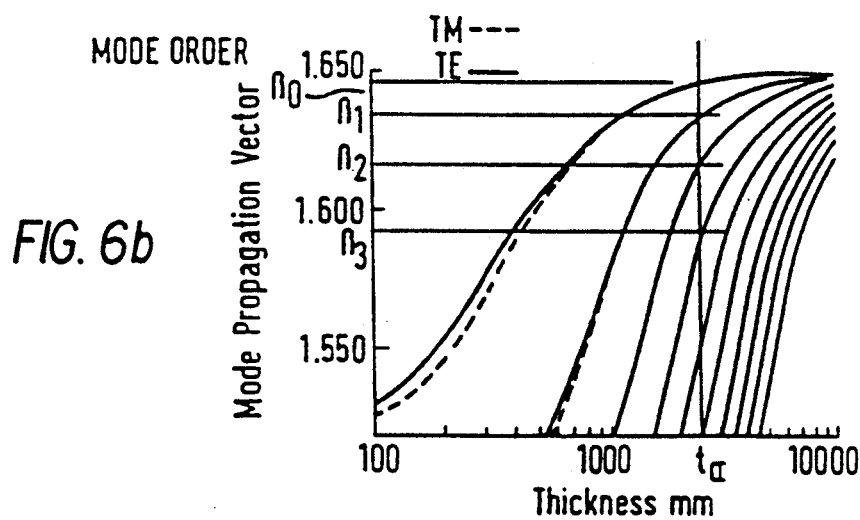
Figure 6C:
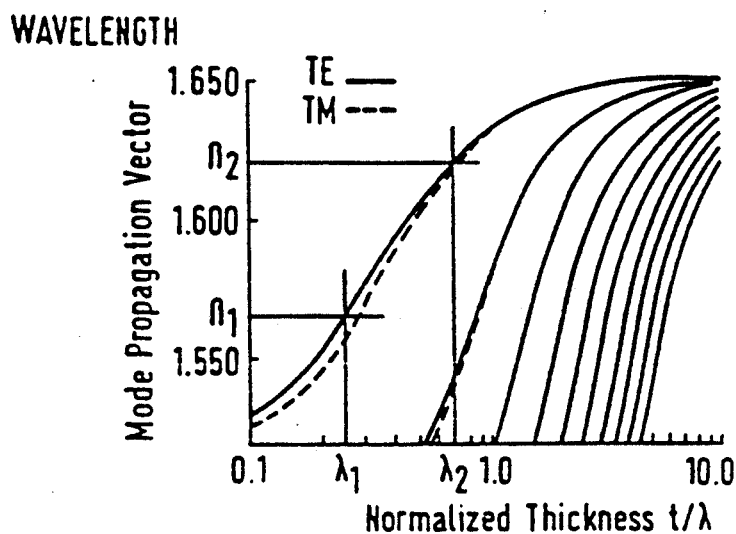
Figure 7A:
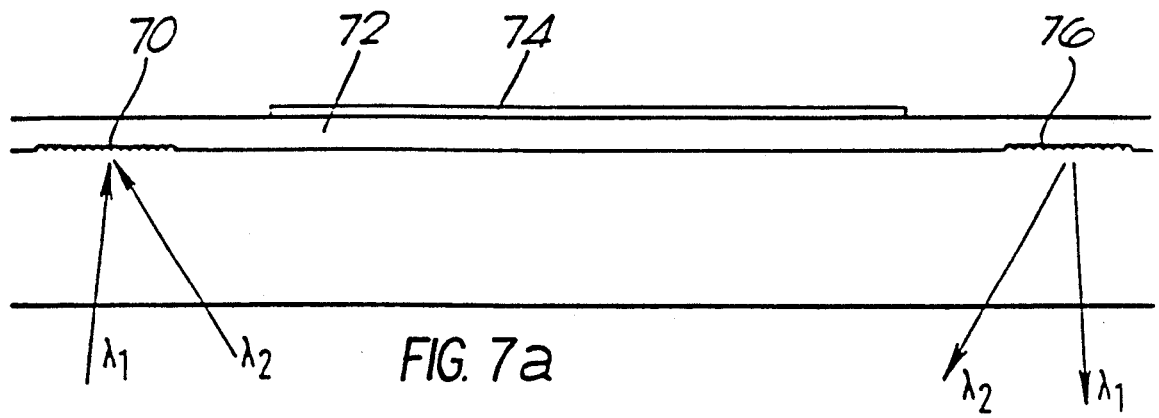
Figure 8A:
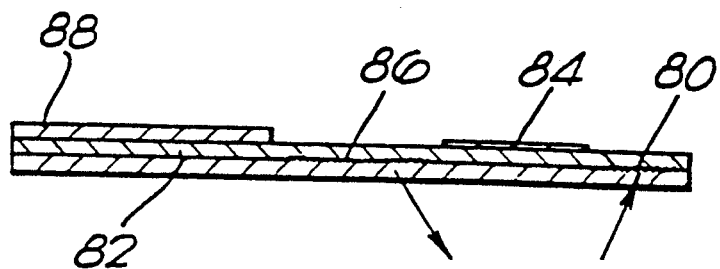

FIG. 5 shows a waveguide using intrawaveguide focusing and incident signal direction discrimination FIGS. 6(a), 6(b), 6(c) show the variation in mode propagation vector of radiation propagation along a waveguide, FIG. 7(a) shows a waveguide employing two different wavelengths of exciting radiation, 7(b) shows the absorption peaks at different wavelengths for use in multiple analyte assays, 7(c) shows a shift in absorption of a single analyte, FIG. 8(a) shows an elevation view of a circular planar waveguide, 8(i b) shows a plan view of the a circular planar waveguide.

Figure 9A:
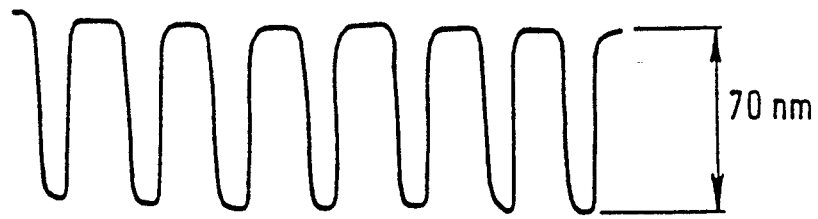
Figure 9B:
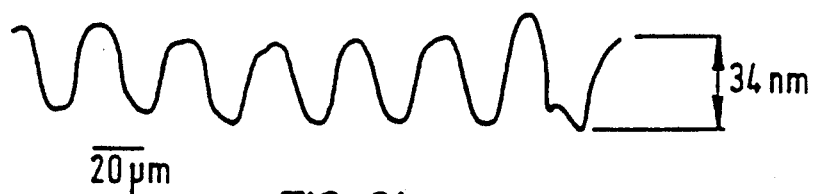

FIG. 9 shows (a) a profile of a photolithography mask and (b) the grating profile which results according to the method exemplified hereinafter in Example 1.

Figure 10:
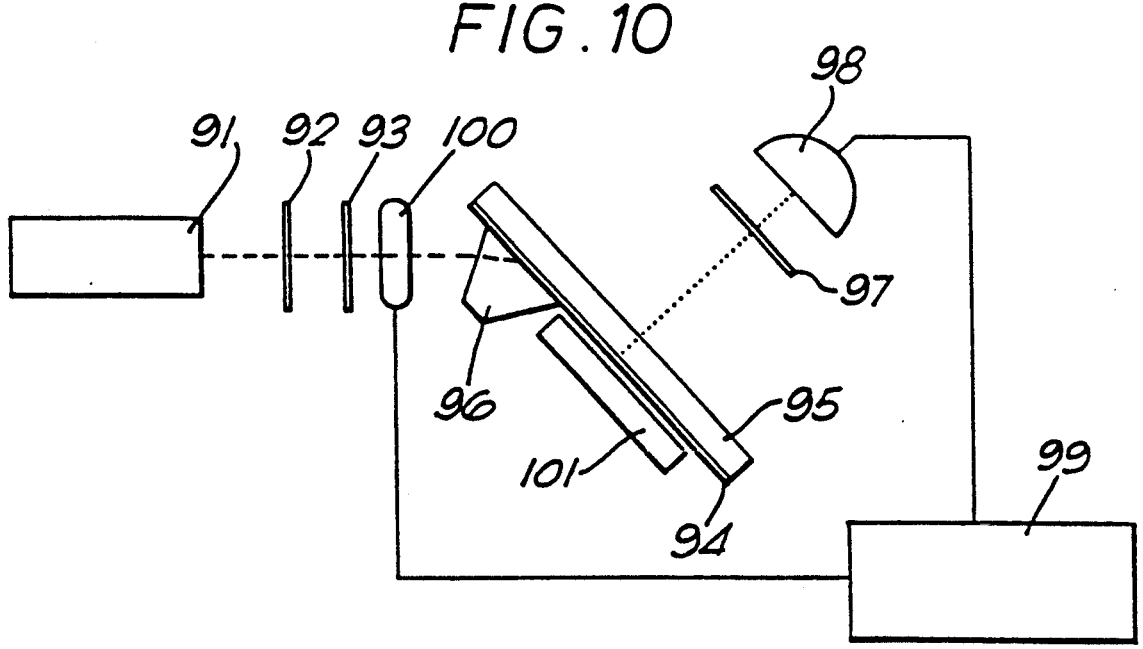

FIG. 10 shows schematically an apparatus suitable for carrying out an assay in connection with the present invention, as exemplified hereinafter in Example 2.

Figure 1A:
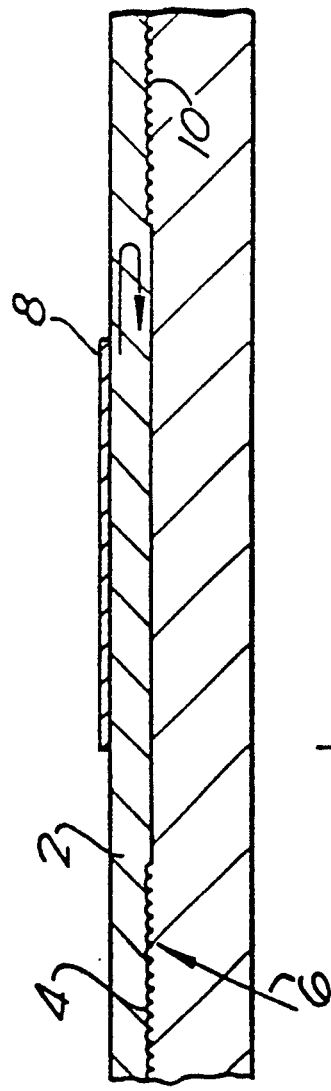
FIG. 1(a) shows a waveguide with grating structures serving to input-couple radiation into the waveguide and reflect radiation propagating along the waveguide.
Figure 1B:
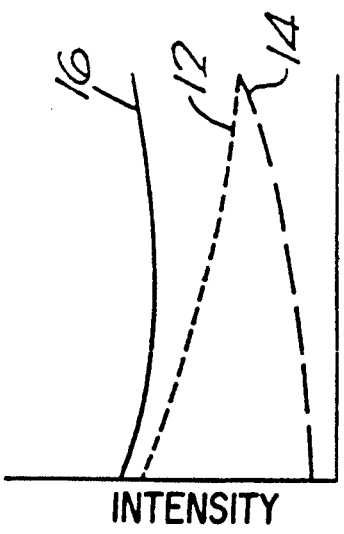
FIG. 1(b) shows a graph of radiation intensity versus position along the transduction region of the device of FIG. 1(a).

FIG. 1(a) shows a waveguide 2 with a grating 4 358 at one end providing input coupling of the exciting radiation 6. The grating 4 exhibits angular discrimination of wavelength and mode order thereby permitting a high degree of control over the excitation process. A transduction region 8 is disposed on the surface of the waveguide 2. A grating 10 provides selective reflection of the exciting radiation. Thus the exciting radiation traverses the transduction region 8 twice, thereby increasing and making more uniform the radiation intensity in the transduction region. The radiation is attenuated by absorption as it propagates along the waveguide 2 as is shown in the graph of radiation intensity versus position along transduction region in FIG. 1 (b). This graph shows the attenuation for both the first pass 12 and second pass 14 of the radiation together with the resulting total intensity 16.

Figure 2:
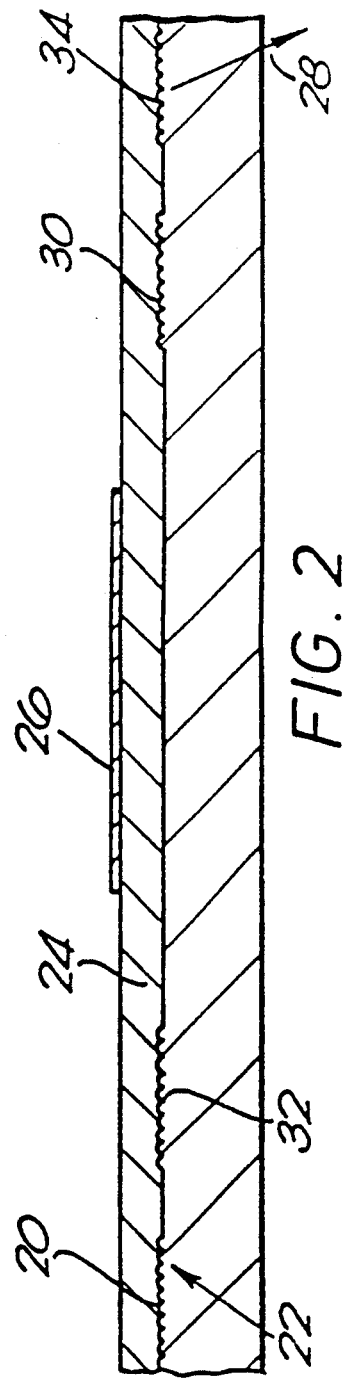
FIG. 2 shows a waveguide with grating structures providing both input-and output-coupling and wavelength selective reflection.

FIG. 2 illustrates another waveguide configuration A grating 20 input-couples the exciting radiation 22 into the waveguide 24. The transduction region 26 is such that signal radiation 28 (such as that emitted by bound fluorophore) of a different wavelength to the exciting radiation 22 is coupled into the waveguide 24. A second grating 30 selectively reflects the exciting radiation 22 and as described above increases and makes more uniform the intensity of the exciting radiation of the transduction region 26. Another grating 32 selectively reflects the signal radiation 28. A further grating 34 output-couples the signal radiation from the waveguide 24. Grating 32 serves to increase the amount of signal radiation 28 reaching grating 34 and thus being output-coupled from the waveguide 24. Grating 30 also serves to reduce the amount of exciting radiation 22 reaching the grating 34.

If the signal radiation 28 differs in mode or polarisation from the exciting radiation 22 then gratings 30 and 32 could be used to reflect specific polarisations or modes of the radiation.

Grating 32 could also incorporate an output-coupling function for the exciting radiation 22. If, say, 5% of the exciting radiation 22 within the waveguide 24 were output-coupled by grating 32 then this could be used as a reference signal for calibration/scaling.

Figure 3B:
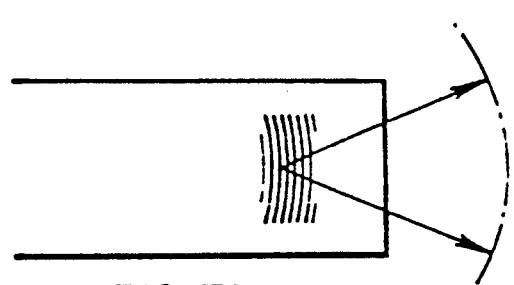
Figure 3C:
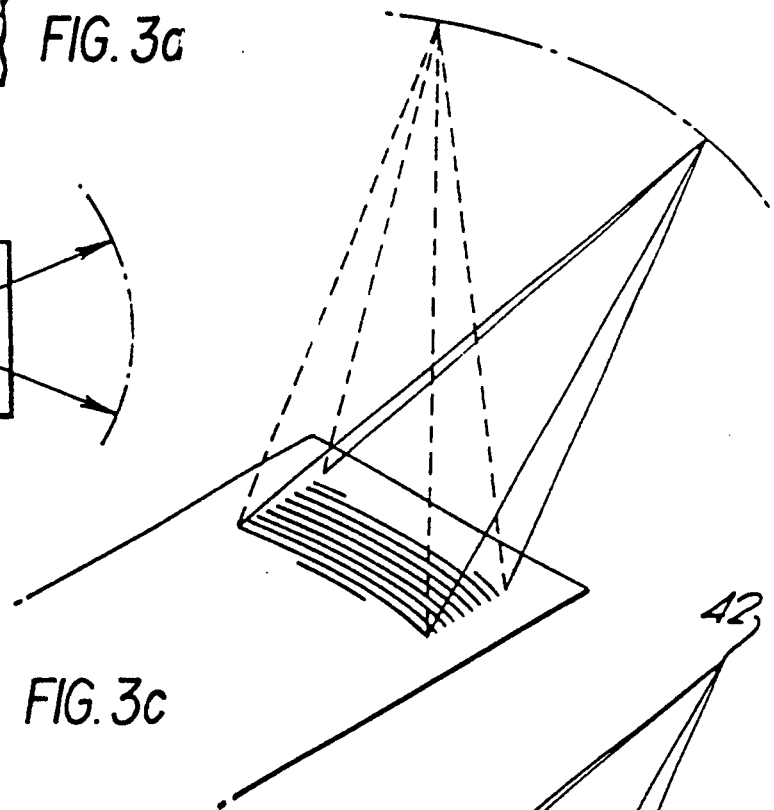

The use of gratings to deform spatially the radiation within the waveguide is illustrated in FIGS. 3(a), (b) and (c). These figures illustrate how it is possible to achieve angular discrimination between wavelengths, polarisations, mode orders and the incidence direction of radiation. FIG. 3a shows angular discrimination in the plane perpendicular to the waveguide. FIG. 3b shows angular discrimination in the plane parallel to the waveguide. FIG. 3c shows how radiation of differing wavelength/mode/polarisation may be focused to different points outside the waveguide. Radiation may also be focused to a point within the waveguide as is shown in FIG. 5.

FIG. 4 illustrates a simple application of the property shown in FIG. 3. Grating 40 is used to input-couple exciting radiation originating from a point source 42 into a waveguide 44 (no external optics are needed). The exciting radiation then traverses the transduction region 46 and reflects off grating 48.

FIG. 5 shows a waveguide using intra-waveguide focusing. Exciting radiation from point source 50 is input-coupled to the waveguide 52 by grating 54. Grating 54 also has the function of causing the radiation to converge. The radiation then traverses transduction region 56. The radiation reflects off grating 58, the radiation having a focal point within the waveguide 52 at a point which also happens to be within grating 58. The radiation then once more traverses the transduction region 56 to reach grating 60. Grating 60 serves to output-couple the radiation from the grating 58 and focus it to a point 62.

FIG. 6 shows the variation in mode propagation vector of radiation propagating along a waveguide with waveguide thickness for differing polarisations, mode orders and wavelengths. The discrimination of the grating structures described above is achieved by exploiting the phenomena illustrated in these graphs so that the grating structures selectively interact with radiation having certain propagation characteristics. Where the interaction in the transduction region is dependent on mode order/polarisation/wavelength then the differential analysis of the signals for a set of modes is a useful method of detection when the waveguide modes can be accurately controlled.

Figure 7B:
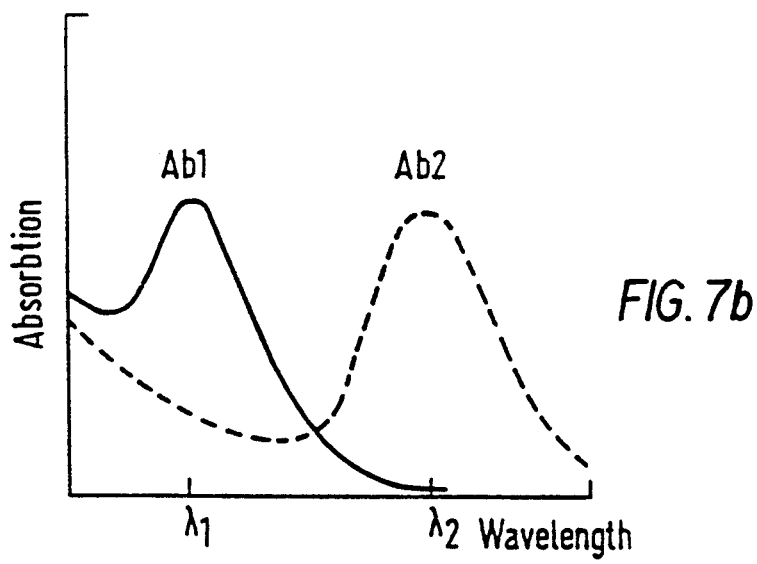
Figure 7C:
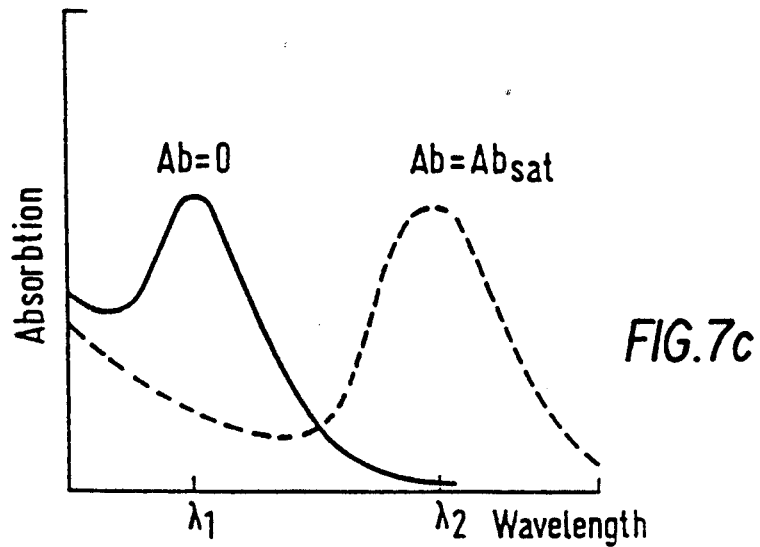

A waveguide employing two different wavelengths of exciting radiation is shown in FIG. 7(a). Exciting radiation with wavelength $i\lambda_1$ is input-coupled at a first angle by grating 70 whilst exciting radiation with a different wavelength $\lambda_2$ is input-coupled at a second angle by grating 70. The radiation then propagates along the waveguide 72, traverses the transduction region 74 and is output-coupled by grating 76 at an angle dependent on wavelength. Absorption peaks at different wavelengths for use in multiple analyte assays are shown in FIG. 7(b). Alternatively a shift in absorption of a single analyte could be monitored as illustrated in FIG. 7(c).

Figure 8B:
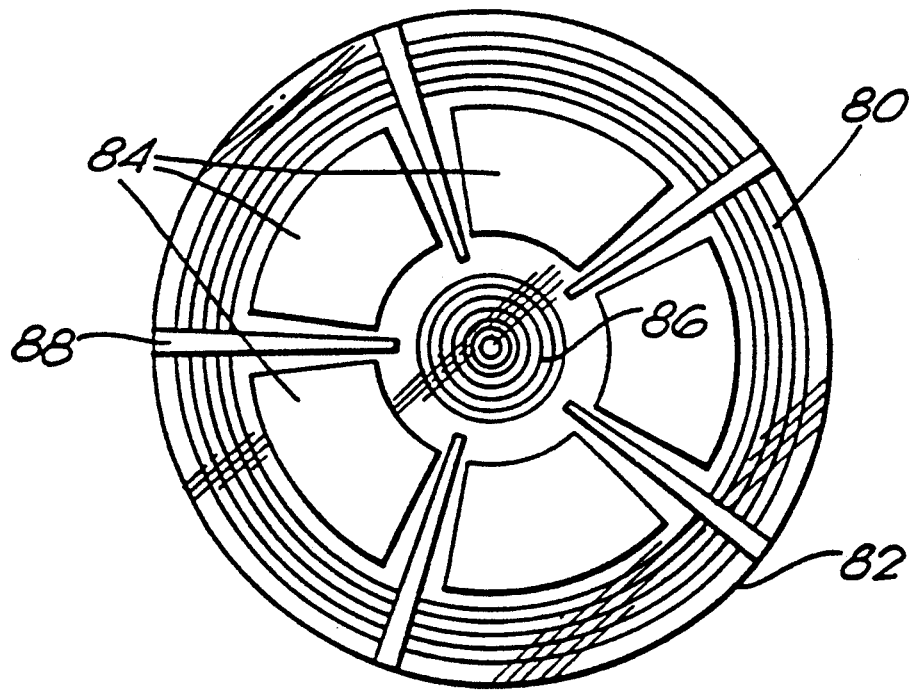

FIG. 8 shows a waveguide with a circular planar geometry. FIG. 8(a) is an elevation; FIG. 8(b) is a plan view. Exciting radiation is input-coupled by grating 80 then propagates towards the centre of the waveguide 82. The radiation traverses transduction region 84 and is output-coupled by grating 86. Strips 88, which may be made of glue, separate the different transduction regions. This waveguide is particularly suited to the use of multiple transduction regions and can also benefit from the intensity profile of focused radiation to reduce the effect of absorption as described above.

The examples above illustrate only some of the large number of waveguide configurations made possible using the invention and many alternative embodiments will be apparent to those skilled in the art.

The following non-limiting Examples illustrate aspects of the present invention.

EXAMPLE 1

Fabrication of a grating on a glass waveguide

A general method for fabricating thin-film optical waveguides on glass substrates at low cost has been described in the literature (A. N. Sloper & M. T. Flanagan, Electronics Letts. 24, 353–355 (1988)).

A solution of 1M iron (III) nitrate (BDH, Poole, UK), 1M phosphoric acid (BDH, Poole, UK) and methanol (BDH, Poole, UK) was applied to a large face of a glass microscope slide having dimensions 52 mm×75 mm×1.5 mm (Gallenkamp, UK). The coated slide was spun at 1000 rpm for 2 minutes. Immediately after spinning, a photolithography mask having a rectangular grating profile of pitch approximately 21 micrometers and depth 70 nm (RAL, Daresbury, UK) was pressed using finger pressure into the iron (III) phosphate film, which was still soft, on the glass side. The coated slide was then baked for 1 hour at 200° C. The resulting hard glassy film on the slide was found to have a refractive index of 1.72. The surface profile (Taly step trace) of the grating is shown diagrammatically in FIG. 9(b), below a profile of the photolithography mask described hereinabove, for comparison, FIG. 9(a).

Embossed iron (III) phosphate films of the type described may be used either as overlays on a waveguide surface or as intrinsic waveguides when deposited on substrates having a refractive index less than 1.72 (e.g. Permabloc, Pilkington Glass Ltd., St. Helens, UK).

An appropriate reagent can be immobilised on a transduction region of the waveguide in conventional manner.

EXAMPLE 2

Assay of human chorionic gonadotrophin (hCG)

A waveguide fabricated according to Example 1 may be used in the assay to be described, wherein fluorescently labelled antibody becomes bound as a result of formation of a sandwich complex with the analyte ligand (hCG) and a second antibody already immobilised at the transduction region of the waveguide surface.

Preparation of Starting Materials (i) Fabrication of anti-hCG antibody-coated waveguide After thorough washing with detergent and ultrasonic agitation, the transduction region of a waveguide fabricated according to the method of Example 1 is activated with a silane (8% 3-glycidoxypropyltrimethoxysilane) at pH 3.5 for 2 hours. The transduction region is then washed and an appropriate crosslinking agent (e.g. SMCC, succinimidyl 4-(N-maleimidomethyl)cyclohexane-1-carboxylate, or glutaraldehyde) is used to couple anti-hCG antibody to the surface using standard techniques (see, for example, Ishikura et al, Journal of Immunoassay 4, 209–327 (1983)). The waveguide is then spin-coated with a 10% sucrose, 0.1% casein layer and stored under dry conditions at 4° C. until use.

(ii) Preparation of XRITC-conjugated anti-hCG antibody

Monoclonal anti-hCG antibodies are obtained from mouse ascites fluid by the method of Milstein and Kohler in Nature 256, 495–497 (1975). Antibodies from individual hybridoma cell lines are screened to identify those producing antibody to discrete antigen determinants. Antibodies having the highest affinities to hCG are selected for use in the assay. 20 mg of XRITC are dissolved in 2 ml of methanol and the resulting solution is made up to 20 ml with a buffer solution of 0.2M sodium bicarbonate (pH9). This solution is then mixed with 2 mg of anti-hCG antibody and left to react for 19.5 hours. Finally, the solution is purified using a Pharmacia PD10 column and employing 0.2M sodium bicarbonate buffer.

(iii) Preparation of hCG standard solution

A freeze-dried preparation of hCG, calibrated against the first international reference preparation (75/537) is diluted in a phosphate buffer solution (pH 7.3) to the desired concentration.

Apparatus and Optical Measurement

Apparatus suitable for carrying out an assay using the above starting materials is shown schematically in FIG. 10. The light source 91 is a 1 mW helium/neon laser (Melles Griot, USA) producing a beam of radiation at 543.5 nm. The beam passes through an interference filter 92 (546.1 nm, bandwidth 10 nm) and then through a polariser 93, in order selectively to excite the TE mode of the optical waveguide 94, which is present on the surface of a substrate 95. Mounted on the waveguide is a prism 96 (an equilateral prism of LAF788474 glass having a refractive index of 1.792 at 543.5 nm (IC Optical Systems, Beckenham, UK)). Fluorescence signal produced during the assay is filtered by a long-pass collection filter 97 with a cut-on at 600.2 nm (Ealing Electro-optics, Ealing, UK) and is then detected by a Hakuto R928 photomultiplier tube 98 (Hakuto, Waltham Cross, UK). An EG and G 5207 lock-in amplifier 99 is used to retrieve the signal from the photomultiplier tube and is connected to a chopper 100 which modulates the laser output. A glass cover 101 is used to form a cell cavity of sufficiently small dimensions to enable sample to be drawn into contact with the transduction region of the waveguide by capillary action.

The apparatus is calibrated by recording the signal from the photomultiplier tube 98 at 30 second intervals over a period of 8 minutes for zero and known concentrations of hCG and at a fixed, known concentration (excess) of XRITC-conjugated anti-hCG antibody Assays are then carried out by following the same procedure, but using analyte solutions in which the concentrations of hCG are unknown, and comparing the results with the calibration curves.

We claim:

1. A planar waveguide comprising an input grating structure constructed so as to couple excitation radiation into the waveguide so as to propagate therethrough, a reflecting grating structure spacially disposed from said input grating structure and constructed so as to reflect said excitation radiation propagating within the waveguide, and a transduction region located between said input grating structure and said reflecting grating structure, whereby during use said excitation radiation traverses said transduction region at least twice.

2. A waveguide according to claim 1 having a thickness of 0.2 to 10.0 microns.

3. A waveguide according to claim 1 further comprising an output grating structure constructed so as to couple signal radiation out of the waveguide, whereby during use said signal radiation results from excitation of the transduction region and has a wavelength different from said excitation radiation.

4. A waveguide according to claim 3 further comprising a second reflecting grating structure constructed so as to reflect said signal radiation propagating within the waveguide.

5. A waveguide according to claim 1 which is substantially circular with a plurality of said input and reflecting grating structures and said transduction regions disposed concentrically.

6. A waveguide according to claim 1 further comprising at least one grating structure constructed so as to be able to filter, focus, defocus or collimate radiation.

7. A waveguide according to claim 1 wherein said transduction region has immobilized thereon, directly or indirectly, a material capable of specifically binding to a species to be assayed.

8. A waveguide sensor useful for the optical assay of a chemical, biological or biochemical substance, said waveguide sensor comprising a planar waveguide comprising an input grating structure constructed so as to couple excitation radiation into the waveguide so as to propagate therethrough, a reflecting grating structure spacially disposed from said input grating structure and constructed so as to reflect said excitation radiation propagating within the waveguide, and a transduction region located between said input grating structure and said reflecting grating structure, said transduction region having immobilized thereon, directly or indirectly, a reagent constructed so as to interact with another assay reagent during use so as to produce an optically measurable result, whereby during use said excitation radiation traverses said transduction region at least twice.

9. A waveguide sensor according to claim 8 useful for the optical assay of a ligand in a sample, wherein the reagent immobilized on the transduction region is either a specific binding partner for the ligand or a ligand analogue.

10. A waveguide sensor according to claim 9 wherein said waveguide further comprises an output grating structure constructed so a to couple signal radiation out of the waveguide, whereby said signal radiation has a wavelength different from said excitation radiation.

11. A waveguide sensor according to claim 10 wherein said waveguide further comprises a second reflecting grating structure constructed so as to reflect said signal radiation propagating within the waveguide.

12. A waveguide sensor according to claim 8 wherein said waveguide is substantially circular with a plurality of said input and reflecting grating structures and said transduction regions disposed concentrically.

13. In a method of assaying for a ligand in a sample which method comprises incubating the sample with components (a) a specific binding partner for the ligand and (b) a ligand analogue or a specific binding partner for the ligand, one of said components being immobilised on the surface of a transduction region of a planar waveguide and the other of said components carrying a fluorophore, said fluorophore becoming bound to said transduction region as a result of complex formation; propagating excitation radiation in the waveguide so as to cause said bound fluorophore to emit signal radiation into the waveguide; and measuring said signal radiation to determine the presence or amount of said ligand; the improvement wherein said waveguide comprises an input grating structure constructed so as to couple excitation radiation into the waveguide so as to propagate therethrough, a reflecting grating structure spacially disposed from said input grating structure and constructed so as to reflect said excitation radiation propagating within the waveguide, and said transduction region being located between said input grating structure and said reflecting grating structure, whereby during said assay said excitation radiation traverses said transduction region at least twice.

14. The method of claim 13 wherein said waveguide additionally comprises an output grating structure constructed so as to couple signal radiation out of the waveguide.

15. The method of claim 14 wherein said waveguide additionally comprises a second reflecting grating structure constructed so as to reflect said signal radiation propagating within the waveguide.

16. In a method of assaying for a ligand in a sample which method comprises incubating the sample with components (a) a specific binding partner for the ligand and (b) a ligand analogue or a specific binding partner for the ligand, one of said components being immobilised on the surface of a transduction region of a planar waveguide, the immobilised component or the surface of the transduction region having a fluorophore bound thereto, and the other of said components being such that on complex formation the signal radiation emitted by said fluorophore is quenched; propagating excitation radiation into the waveguide so as to cause said fluorophore to emit signal radiation into the waveguide; and measuring the extent to which said signal radiation is quenched to determine the presence or amount of said ligand; the improvement wherein said waveguide comprises an input grating structure constructed so as to couple excitation radiation into the waveguide so as to propagate therethrough, a reflecting grating structure spacially disposed from said input grating structure and constructed so as to reflect said excitation radiation propagating within the waveguide, and said transduction region being located between said input grating structure and said reflecting grating structure, whereby during said assay said excitation radiation traverses said transduction region at least twice.

17. The method of claim 16 wherein said waveguide additionally comprises an output grating structure constructed so as to couple signal radiation out of the waveguide.

18. The method of claim 17 wherein said waveguide additionally comprises a second reflecting grating structure constructed so as to reflect said signal radiation propagating within the waveguide.

* * * * *